(12) United States Patent
Barry et al.

(10) Patent No.: US 6,175,420 B1
(45) Date of Patent: Jan. 16, 2001

(54) OPTICAL SENSORS FOR CELL PROCESSING SYSTEMS

(75) Inventors: Donald Barry, Norwood; Glen Jorgensen; Bruce H. Edwards, both of Marlboro; Jeremy Fennelly, Watertown, all of MA (US)

(73) Assignee: ZymeQuest, Inc., Beverly, MA (US)

( * ) Notice: Under 35 U.S.C. 154(b), the term of this patent shall be extended for 0 days.

(21) Appl. No.: 09/082,086

(22) Filed: May 20, 1998

Related U.S. Application Data

(60) Provisional application No. 60/047,213, filed on May 20, 1997.

(51) Int. Cl.[7] .................................................. G01N 21/59
(52) U.S. Cl. .............................. 356/436; 356/39; 436/164
(58) Field of Search ........................... 356/39, 425, 436; 436/164

(56) References Cited

U.S. PATENT DOCUMENTS

| | | | |
|---|---|---|---|
| D. 337,388 | 7/1993 | Nilsson et al. | D24/224 |
| 4,155,483 | * 5/1979 | Bartlett et al. | 222/1 |
| 4,227,814 | 10/1980 | Soodak et al. | 356/410 |
| 4,810,090 | 3/1989 | Boucher et al. | 356/39 |
| 5,064,282 | 11/1991 | Curtis | 356/40 |
| 5,318,512 | 6/1994 | Neumann | 604/6 |
| 5,356,392 | * 10/1994 | Firth et al. | 604/198 |
| 5,385,539 | 1/1995 | Maynard | 604/4 |
| 5,386,734 | 2/1995 | Pusinelli | 73/863 |
| 5,449,622 | * 9/1995 | Yabe et al. | 436/164 |
| 5,505,685 | 4/1996 | Antwiler | 494/37 |
| 5,612,207 | * 3/1997 | Nicolau et al. | 435/173.6 |
| 5,734,464 | 3/1998 | Gibbs | 356/39 |

FOREIGN PATENT DOCUMENTS

| | | | |
|---|---|---|---|
| 0 682 953 A1 | 11/1995 | (EP) | A61M/1/36 |
| WO96/28199 | 9/1996 | (WO) | A61M/1/36 |

OTHER PUBLICATIONS

Burr–Brown, OPT 210 "Monolithic Photodiode and Amplifier" (PDS–1313A), Dec. 1995.
Purdy Electronics Corporation, AND176RAG "Dual Color High Brightness LED", Jan. 1998.
Communication from the International Searching Authority dated Jul. 9, 1998 (6 pages).

* cited by examiner

Primary Examiner—F. L. Evans
Assistant Examiner—Zandra V. Smith

(57) ABSTRACT

An optical sensor is disclosed for use in an interactive cell processing system that includes a plurality of sensors arranged for monitoring and providing sensor data to a control module that directs processing of biological cells. The sensors including an optical sensor for characterizing a fluid transferred in a sterile manner during the processing. The optical sensor includes a light source, a light detector, a cuvette and a control circuit. The light source is connected to a control circuit and is constructed and arranged to emit light of at least one selected wavelength directed toward the fluid. The cuvette is constructed as a part of a fluid distribution manifold that includes several conduits for transferring the sterile fluid during the processing, wherein the cuvette is constructed and arranged to convey the fluid. The light detector is connected to the control circuit and is constructed and arranged to detect light that was emitted from the source and has interacted with the fluid flowing inside the cuvette. The control circuit is constructed and arranged to characterize the fluid in the cuvette based on the detected light.

4 Claims, 12 Drawing Sheets

AUTOMATED INTERACTIVE CELL PROCESSING SYSTEM

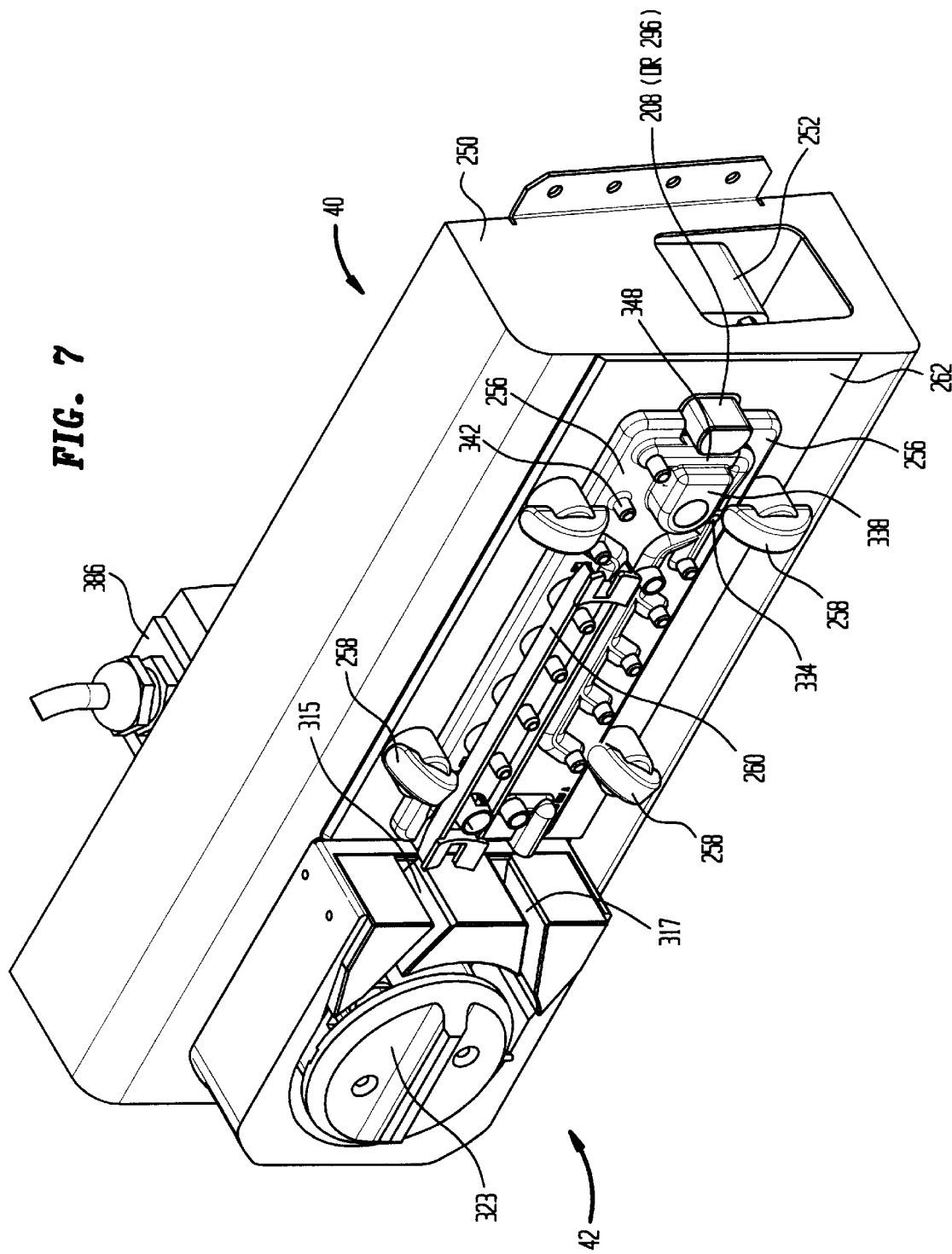

OPTICAL SENSORS FOR CELL PROCESSING SYSTEMS

RELATED APPLICATIONS

This application claims the benefit under Title 35, U.S.C. §119(e) of U.S. Provisional Application Ser. No. 60/047,213, filed May 20, 1997, now abandoned, entitled "Cell Processing System", incorporated herein by reference. This application is also related to co-pending U.S. patent applications entitled: "Rotating Seals for Cell Processing Systems", application Ser. No. 09/081,733, filed on May 20, 1998; "Apparatus and Method for Expressing Fluid Materials", application Ser. No. 09/082,200 filed May 20, 1998, now abandoned; "Fluid Management Systems", application Ser. No. 09/082,201 filed on May 20, 1998; and "Cell Processing Systems", application Ser. No. 09/082,341, filed on May 20, 1998, now abandoned, all of which are incorporated by reference.

FIELD OF THE INVENTION

The invention relates to an optical method and apparatus for use in an interactive cell processing system.

BACKGROUND OF THE INVENTION

Cell processing includes steps where cells or cell elements are treated with different process chemicals or are washed and then separated from a liquid phase. For example, when preparing frozen erythrocytes for transfusion, erythrocytes are separated from cryopreservatives and other blood components such as white cells, platelets and sub-cellular debris. The entire process must be performed under sterile conditions that minimize the risk of contamination. Furthermore, whole blood is separated into its various therapeutic components such as red blood cells, white blood cells, platelets and plasma which are later transfused. There are different cell processing systems that process biological cells in an automated or semi-automated way. These systems may use a controller connected to various sensors and valves for controlling the process and helping an operator to maximize the processing efficiency. However, these systems do not interactively adjust the process based on the amount or type of the processed cells or different processing conditions.

During the separation, for example, by expression of the processing fluid, it is desirable to accurately differentiate the supernatant (for example, a wash solution) from the harvested cells in order to avoid losing valuable cellular product into the expressed (and thereafter discarded) wash solution. Various optical detectors have been designed and described in the prior art. However, there are several features that needed to be resolved. For example, the means and location of the optic assembly housing can be problematic. A separate plastic cuvette is typically used to provide flat, parallel surfaces through which the object cells must pass. These flat surfaces minimize optical distortion but add a separate object, the cuvette, to the disposable set designed to contain the cells and washing reagents. This additional cuvette increases the complexity and requires an extra operator step during set up of the instrument, as this cuvette must be accurately positioned in the optical detector housing. Any operator interaction may potentially introduce an error. If the housing is located away from the centrifuge, such design leaves a length of tubing between its location and the centrifuge that is full of packed cells immediately after the first of the cells have been detected. These cells are typically lost to the waste supernatant of the next wash cycle. Finally, cell processing may involve separating one cell type from another (e.g., the buffy coat containing white blood cells and platelets must be separated from erythrocytes being prepared as packed red cells for transfusion; erythrocytes must be removed from bone marrow during the preparation of progenitor cells).

Therefore, there is a need for an optical sensor for use in an automated interactive cell processing system. Such optical sensor would need to have a practical design and would need to provide precise and reproducible data for different disposable elements, varying amounts of processed cells, different types of processed cells, or different operators and processing laboratories.

SUMMARY OF THE INVENTION

The present invention is a optical method and apparatus for characterizing a fluid transferred in a sterile manner during cell processing.

In one aspect, an optical sensor is used in an interactive cell processing system that includes a plurality of sensors arranged for monitoring and providing sensor data to a control module that directs processing of biological cells. The sensors including an optical sensor for characterizing a fluid transferred in a sterile manner during the processing. The optical sensor includes a light source, a light detector, a cuvette and a control circuit. The light source is connected to a control circuit and is constructed and arranged to emit light of at least one selected wavelength directed toward the fluid. The cuvette is constructed as a part of a fluid distribution manifold that includes several conduits for transferring the sterile fluid during the processing, wherein the cuvette is constructed and arranged to convey the fluid. The light detector is connected to the control circuit and is constructed and arranged to detect light that was emitted from the source and has interacted with the fluid flowing inside the cuvette. The control circuit is constructed and arranged to characterize the fluid in the cuvette based on the detected light.

The optical sensor may include one or several of the following features:

The light source and the light detector may be arranged in a transmission geometry. The light source, the light detector and the control circuit are enclosed in a housing. The housing is suitable for sterilization by gama rays or by other means.

The fluid distribution manifold includes an integral component constructed to be placed in close proximity to the housing and arranged to define uniquely the position of the cuvette relative to the light source and the light detector.

The cuvette is made of an optical material suitable for sterilization. The cuvette is made of an optical material suitable for sterilization using gama radiation. The cuvette and the fluid distribution manifold may be disposable.

The light source and the light detector are located in a sealed housing constructed and arranged for wet cleaning.

The light source includes a light emitting diode (LED) constructed and arranged to emit light of about 560 nm and about 640 nm. The light detector includes a silicon diode. The optical sensor is arranged to detect red blood cells in the fluid.

The control circuit is constructed to activate the light source and the light detector to perform repeated measurements over a short period of time to increase precision of the characterization. The control circuit is constructed to calibrate operation of the optical sensor after placement of the cuvette.

The optical sensor is further arranged to provide data to the control module to actuate re-distribution of fluids flowing in the conduits.

Another aspect is a method of characterizing a fluid transferred in a sterile manner in a conduit during processing of biological cells in a cell processing system. The method includes conveying the fluid in a cuvette during operation of a cell processing system, wherein the conveying includes distributing the fluid in a fluid distribution manifold that includes several conduits for transferring sterile fluid during the processing, and wherein at least one of the conduits is permanently connected to the cuvette. The method also includes emitting light of at least one selected wavelength generated by a light source; detecting light that was emitted from the source and has interacted with the fluid flowing inside the cuvette; and characterizing the fluid in the cuvette based on the detected light.

Another aspect is a method of controlling operation of a cell processing system comprising a control module, a processing module connected in a sterile manner by a set of conduits to a cell module and to a supply module for providing selected process chemicals, and a plurality of sensors providing process data to the control module also arranged to actuate a plurality of valves regulating flow of the cells and the chemicals in the conduits during the operation. The method includes processing biological cells in the processing module by employing process chemicals including saline; expressing the process chemicals from the processing module; transferring a flow the expressed process chemicals to a waste container via the conduits, wherein at least one of the conduits is permanently connected to and in communication with a cuvette. The method also includes emitting light of at least one selected wavelength generated by a light source; detecting light that was emitted from the source and has interacted with the fluid flowing inside the cuvette; characterizing the fluid in the cuvette based on the detected light; and upon detecting presence of the processed biological cells during the characterization, redirecting the flow to transfer the processed biological cells to a cell container.

Any of the above methods may include one or several of the following:

The emitting includes generating light of about 560 nm and about 640 nm. The re-directing includes temporarily reversing the expressing action performed by the processing module to draw back the detected biological cells, and actuating a valve by the control module. The biological cells include red blood cells.

BRIEF DESCRIPTION OF THE DRAWINGS

FIG. 7 is a perspective view of a fluid distribution module including a partial view the optical sensor of FIG. 5.

DESCRIPTION OF THE PREFERRED EMBODIMENTS

Figure 1:
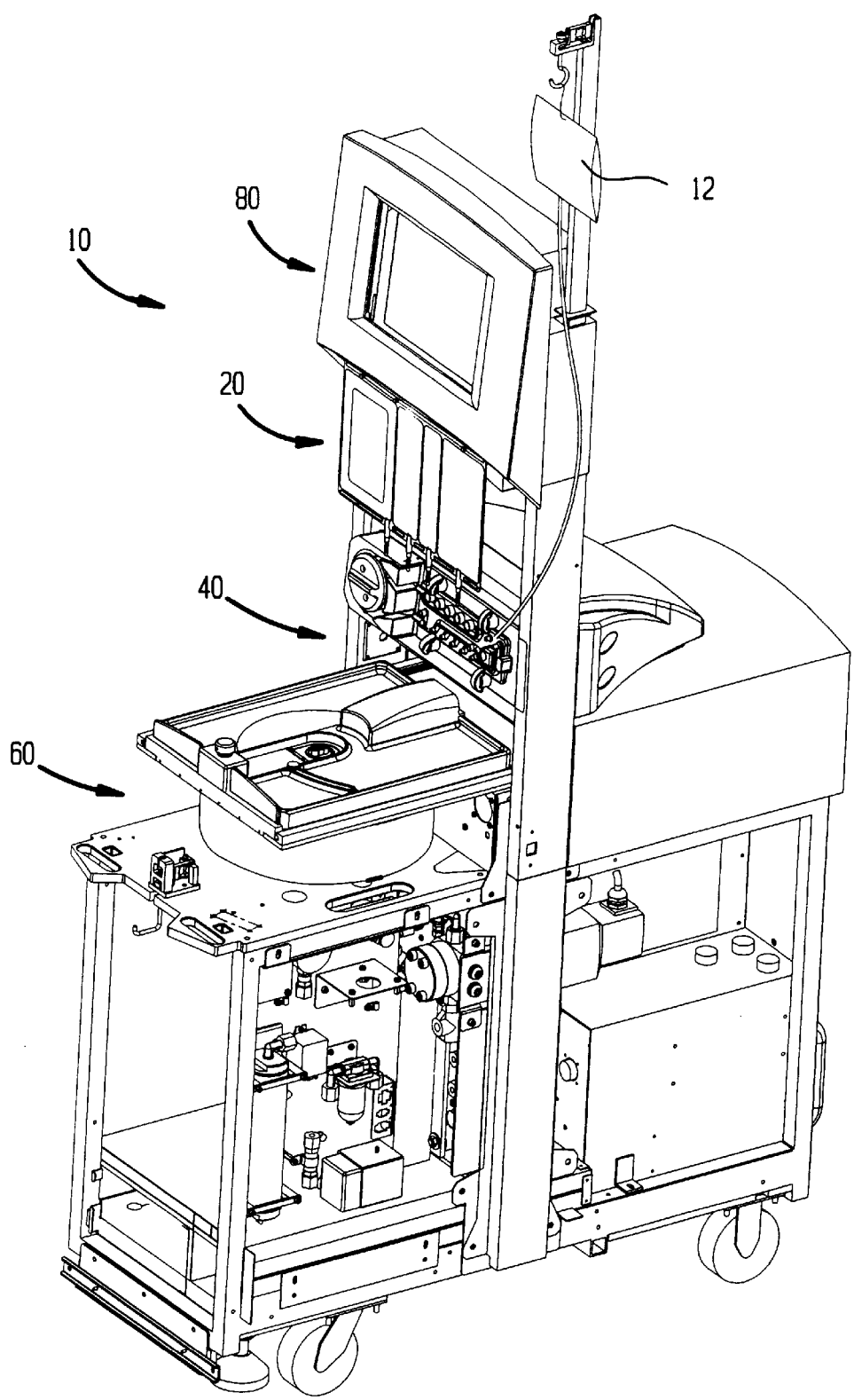
FIG. 1 is a perspective view of an interactive cell processing system.
Figure 3:
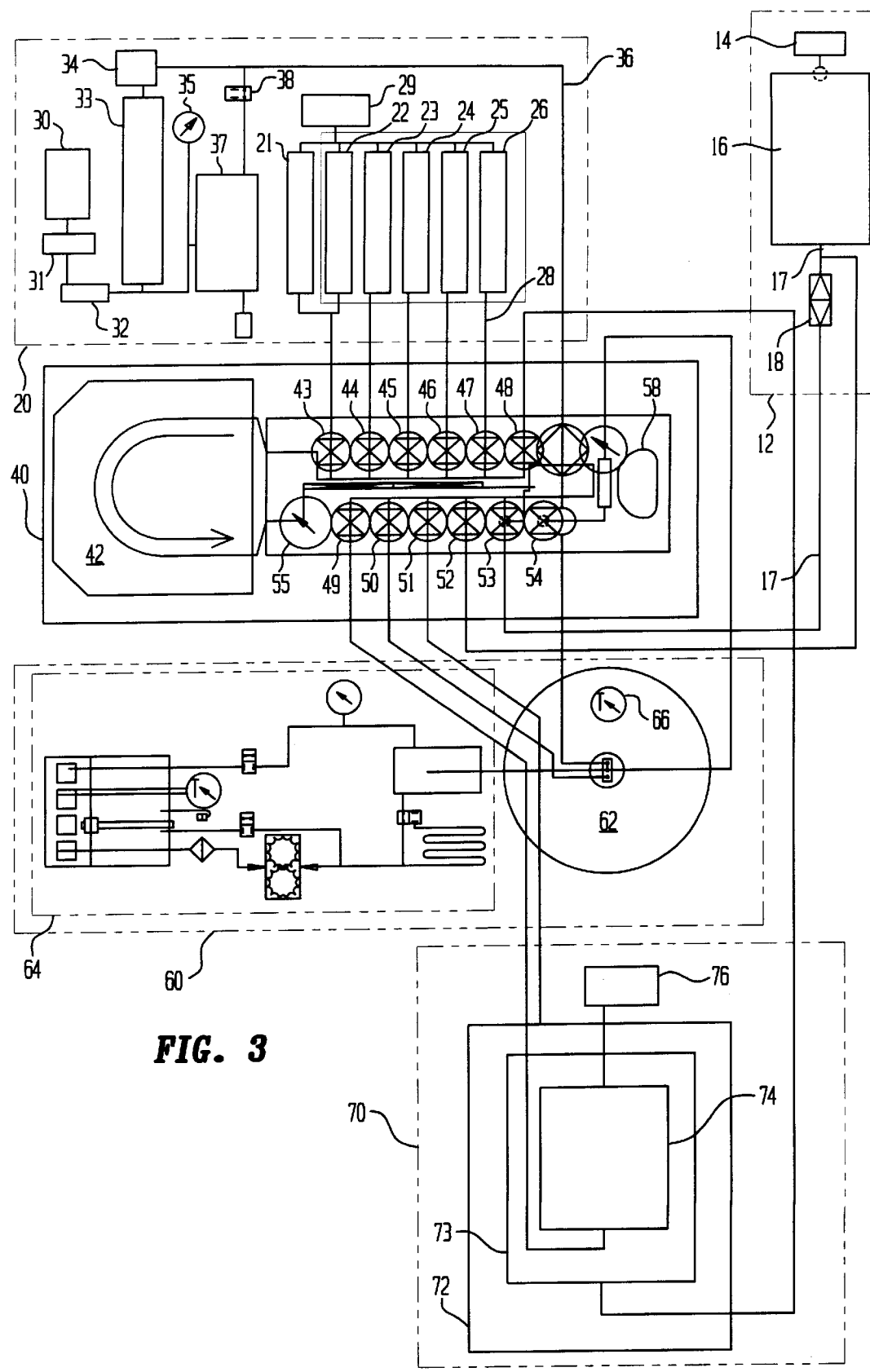
FIG. 3 is a block diagram of the interactive cell processing system of FIG. 1.

Referring to FIGS. 1 and 3, an interactive cell processing system 10 includes a cell module 12, a supply module 20, a fluid distribution module 40, a processing module 60, a collection module 70 (not shown in FIG. 1) and a control module 80. These modules are operatively interconnected for processing biological cells in a sterile environment. Cell module 12 is constructed for a short term or long term storage of biological cells for processing. Supply module 20 includes several containers for storing different process chemicals including saline, or other fluids used for washing the processed cells and also includes sterile air. The containers are connected to fluid distribution module 40 by a set of conduits. Fluid distribution module 40 includes several valves and sensors for dispensing controlled amounts of the process chemicals from supply module 20 to processing module 60 and for dispensing a known amount of the biological cells from cell module 12 to processing module 60. Furthermore, fluid distribution module 40 is constructed to direct the process waste from processing module 60 to a waste container 72 and the processed cells to a cell storage container 74, both of which are located in collection module 70, while maintaining the purity and sterility of the cells. Control module 80 directs the entire process according to a selected algorithm.

Figure 2:
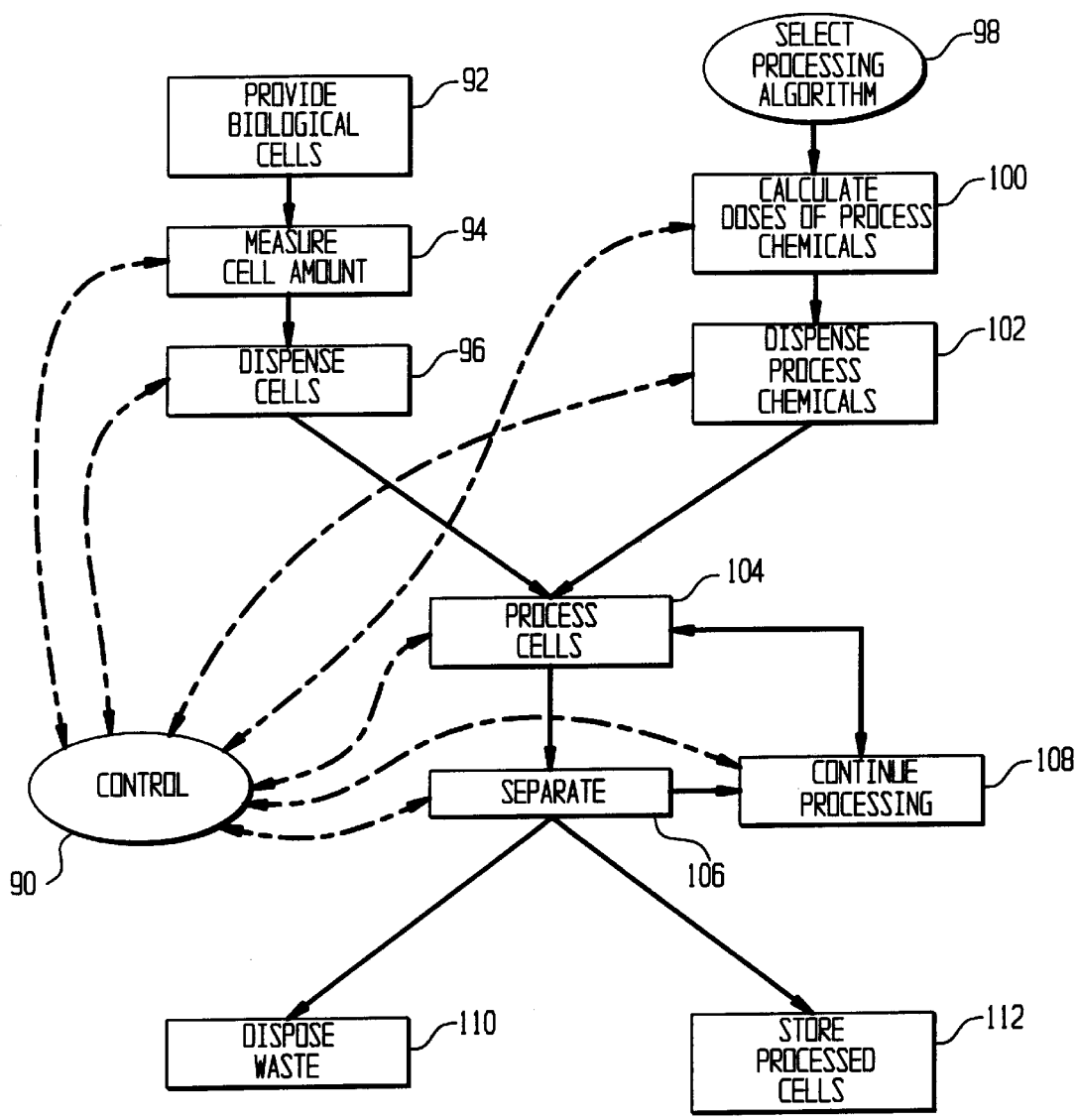
FIG. 2 is a conceptual flow diagram displaying operation of an interactive cell processing system.

In general, the operation of cell processing system 10 is shown in FIG. 2. Control module 80 executes a processing algorithm selected initially (98). Control module 80 includes a logic controller that receives real-time data from several in-line sensors arranged in a processing loop. A mass sensor (or a volume sensor) measures an initial amount of the provided biological cells (94) and sends the data to control module 80. Control module 80 controls the amount of cells dispensed to processing module 60 in accordance with the processing algorithm. Based on the provided amount of the biological cells, control module 80 also calculates the individual doses of the process chemicals (100) and directs a set of control valves to dispense the chemicals (102) in a selected order to processing module 60, again in accordance with the processing algorithm.

Control module 80 executes iteratively the processing algorithm. Control module 80 receives data from the individual sensors (e.g., a weight sensor, a volume sensor, a temperature sensor, an optical sensor, a resistance or capacitance sensor, a flow sensor, a pressure sensor or another sensor arranged to monitor the transferred matter in a liquid, gaseous or solid state). After dispensing the selected amount of one or several processing chemicals to processing module 60, control module 80 regulates the temperature and the time of processing and directs the processing module to agitate, mix or otherwise treat the cells with the process chemicals. Depending on the processing algorithm, control module 80 may manage one or several processing cycles. At the end of each cycle, processing module 60 may separate the processed cells from intermediate products and from the process waste. During the separation process, fluid distribution module 40 detects the fluid component being expressed from processing module 60 and directs the separated components to different containers for disposal (110) or for storage (112). Each processing cycle may use a different processing chemical and different processing conditions. Cell processing system 10 can also process different types of cells at the same time or sequentially. Furthermore, cell processing system 10 may also partially process biological cells and then store them in cell storage container 74 (shown in FIG.

3), which may include a temperature control system. The processed cells may be later automatically dispensed from cell storage container 74 and processed using another processing algorithm. The processed cells may also be grown in culture prior to another use.

Based on the starting weight of the biological cells, the controller calculates the dosage of the processing chemicals. Supply module 20 includes a weight sensor 29 for providing the weight of each process chemical to the controller. During the process, the controller confirms that correct amount of each process chemical has been transferred by measuring the change in the weight of the process chemical stored in supply module 20 and the initial weight of the chemical. The process chemicals in a fluid state are pumped through a 0.2 micron filter to assure sterility. A pressure transducer is mounted up-stream from the filter. If the fluids being pumped through the filter have a variable viscosity, the controller will adjust the pumping speed to yield a constant pressure drop across the filter membrane.

Processing module 60 is designed to assure identical processing conditions (e.g., pressure, temperature, mixing, processing time or other) for large and small amounts of the biological cells provided for processing. For this purpose, processing module 60 includes a processing chamber that has a variable volume design. Depending on the volume of the processed cells and other processing chemicals transferred into the processing chamber, the controller changes the chamber volume. The volume change is achieved by a movable wall that may be a membrane. Processing module 60 includes another pressure sensor for measuring the pressure inside the processing chamber and also includes a temperature sensor for measuring the temperature inside the processing chamber. Based on the data from the temperature sensor, a heat transfer system can provide or remove heat from the processing chamber.

Cell processing system 10 may process or separate cells and/or cell elements from different liquids or solids. Such cells and cell elements include, but are not limited to, erythrocytes (i.e., red blood cells); leukocytes (i.e., white blood cells, including lymphocytes, granulocytes, and monocytes); blood cell progenitors (e.g., primitive stem cells, burst forming units, reticulocytes, megakaryocytes, etc.); cell fragments (e.g., platelets, subcellular elements such as nuclei, debris, etc.); epithelial cells; endothelial cells; mesothelial cells; cells of normal tissues (e.g., liver cells, kidney cells, bladder cells, lung cells, pancreatic cells, embryonic cells, fetal cells, etc.); cells of abnormal tissues (e.g., malignant cells), and other.

Referring again to FIG. 3, in one preferred embodiment of the cell processing system, cell module 12 includes a weight sensor 14 arranged to weigh red blood cells provided in a PVC bag 16. Tubing 17 connects bag 16 to a leuko filter 18 and to fluid distribution module 40. Supply module 20 includes a bag 21 with enzyme A1/B, a bag 22 with enzyme A2, a bag 23 with 140 mMolar potassium phosphate dibasic (DPP), a bag 24 with polyethylene glycol (PEG), a bag 25 with storage solution, and a bag 26 with phosphate citrate isotonic (PCI). Fluid bags 21, 22, . . . , 26 are made of cryovac M312. Each bag is connected by tubing 28 to fluid distribution module 40. Weight sensor 29 is constructed to weigh any of the above-mentioned fluids located in supply module 20. Supply module 20 also includes a compressor 30 connected via a filter 31 and a check valve 32 to air reservoir 33, which stores sterile air used for cell processing. Pressure switch and sensor 34 is in communication with air tubing 36, which delivers sterile air to an air filter located in fluid distribution module 40. A regulator 37, connected to a solenoid valve 36, regulates the air pressure provided to fluid distribution module 40 and to processing module 60. Fluid distribution module 40 includes a peristaltic pump 42, and twelve plunger valves 43, 44, . . . , and 54 connected to a set of conduits for distributing the process chemicals and the cells during the automated process. The logic controller can close or open any combination of the twelve valves to redirect the fluid flowing inside the conduits. A pressure sensor 55 measures the fluid pressure during the process, and a optical sensor 58 monitors the fluid to and from processing module 60. Processing module 60 includes a centrifuge 62 and an expressor system 64. An IR temperature sensor 68 monitors the temperature of the process chemicals or the cells located inside centrifuge 62. Collection module 70 includes a waste bag 72, a saline solution bag 74, and a product bag 76. Collection module 70 also includes a weight sensor 76 connected to product bag 76 and arranged to weigh the processed red blood cells.

The controller controls the volume of the processing chamber of centrifuge 62 to assure identical processing conditions for large or small amounts of the red blood cells. The processing chamber includes a flexible wall for containing expresser fluid inside the processing chamber. For small volumes, expresser system 64 pumps expressor fluid into the chamber until the pressure transducer at the chamber signals a full condition. This pre-filling step assures that different amounts of red blood cells are subjected to the same accumulated centrifugal force and mechanical stresses due to packing. Otherwise, smaller amounts would spin longer and pack harder as the expresser fluid fills the processing chamber during the expression step.

During the process, the controller receives input from IR temperature sensor 66, which measures the temperature of the red blood cells and the process chemicals. If the temperature is less than the set point, expressor of system 64 increases the temperature of the expressor fluid. Conversely, if the temperature is greater than the set point, expresser of system 64 decreases the temperature of the expressor fluid. A control loop continuously monitors the temperature of the processed cells.

Processing module 60 also includes a second pressure transducer that monitors the pressure of the sterile air on the rotating seal. If the seal is working, this pressure only fluctuates slightly between established limits. If the pressure drops below the established threshold, a warning condition is initiated that calls for a check of the rotating seal as well as other possible causes of failure.

Expressor fluid system 64 included a third pressure transducer that measures the pressure of the expressor fluid which is an indirect measure of the pressure on the red blood cells. The controller adjusts the expressor pump speed to assure that pressure is within accepted limits and cells are protected from damage. If the pressure is too low, the pump rate is increased to speed up the expression cycle. If the pressure is too high, the controller sends control signals to the pump to slow down in order to protect the processed cells from excessive pressure. This procedure also protects the "sterility" seal of processing module 60 from excessive pressure.

Figure 4:
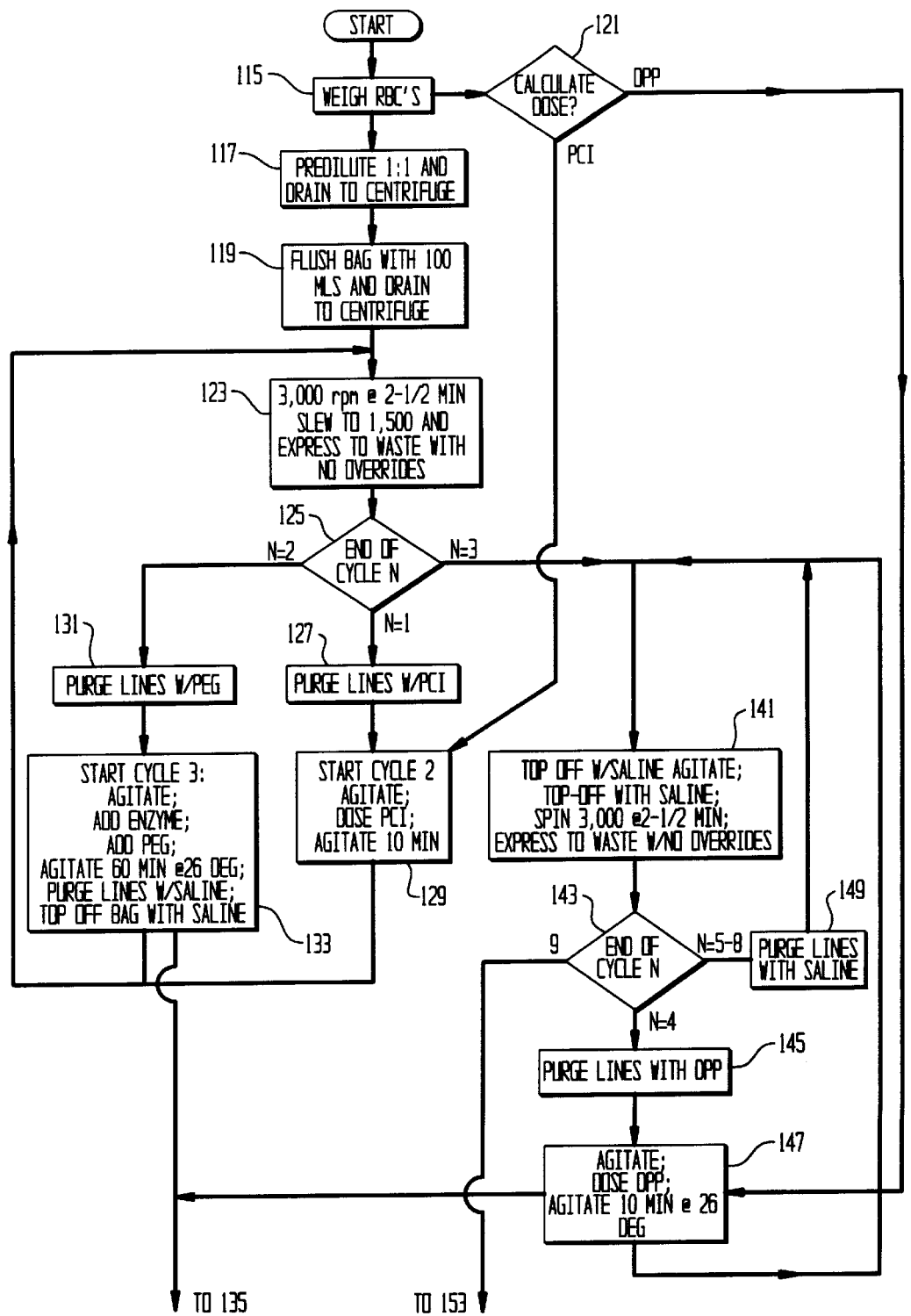
FIGS. 4 and 4A show a flow diagram of a process for enzymatic conversion of red blood cells.
Figure 4A:
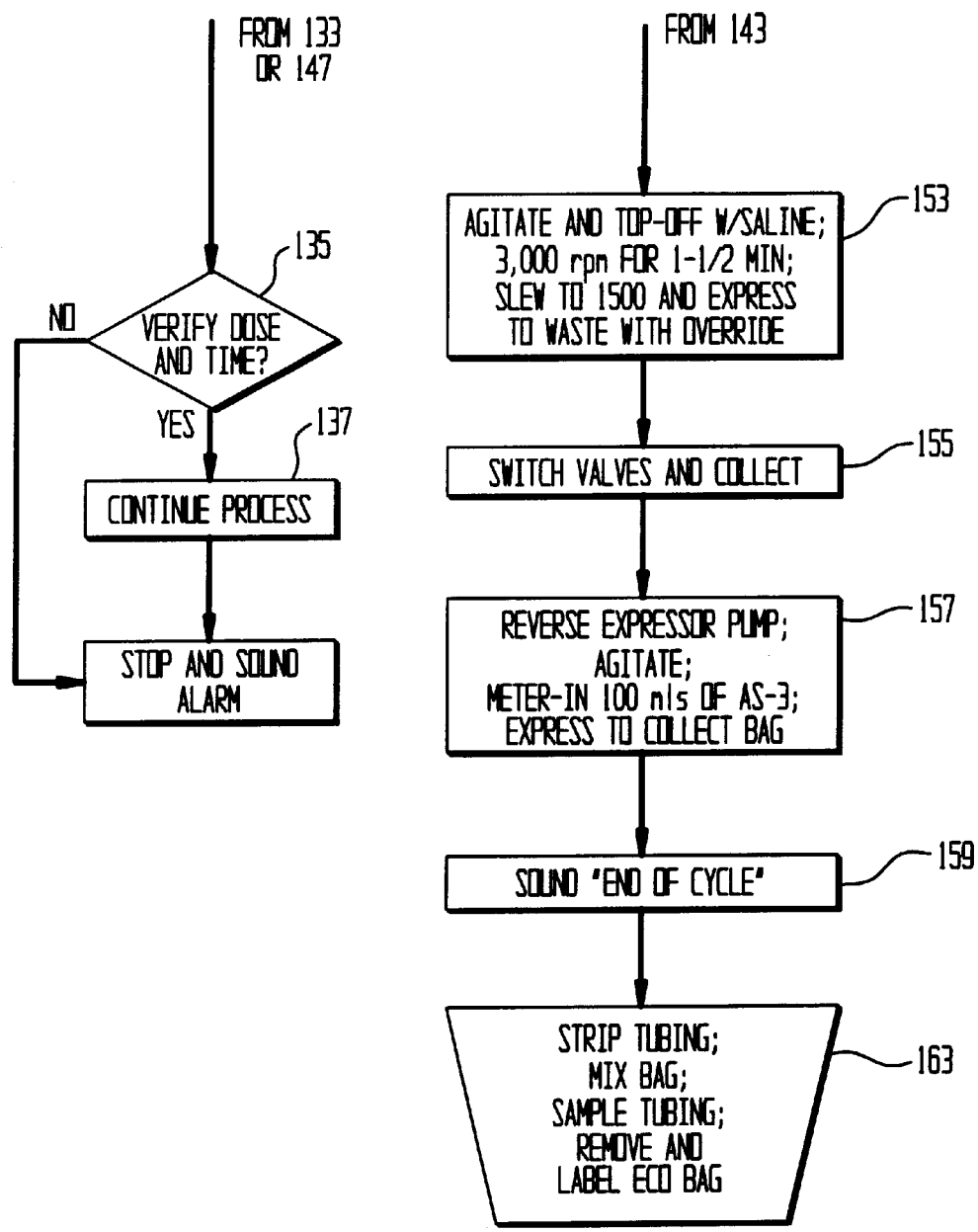

Referring to FIGS. 4 and 4A, in the preferred embodiment, the cell processing system of FIG. 3 is used for enzymatic conversion of red blood cells to type O red blood cells. The enzymatic conversion process starts in step 115 by weighting the provided amount of red blood cells. In step 117, based on the starting weight of the provided red blood cells, the system dilutes the red blood cells dispensed to the processing bag located inside centrifuge 62, shown in FIG.

3, with saline in the 1:1 ratio, and also flushes the bag with 100 ml of saline (step 119). In step 121, the controller calculates the correct dosage of PCI to obtain the ratio of 65 ml of PCI for 100 ml of red blood cells. The controller also calculates the correct dosage of DPP to obtain the ratio of 110 ml of DPP for 100 mls of red blood cells. Prior to executing step 123, the controller confirms that the correct amount of saline was transferred to centrifuge 62. In step 123, the centrifuge spins at 3000 RPM for about 2.5 minutes and then slows down to about 1500 RPM and expresses the saline waste while the washed red blood cells are left in the processing bag.

Next, in step 127, the system purges the tubing with PCI and dispenses the dose calculated in step 121, of PCI to the processing bag. PCI (Phosphate Citrate Isotonic) includes citric acid monohydrate 10.7 g/L, sodium phosphate dibasic (anhydrous) 2.7 g/L, sodium chloride 6.4 g/L suspended in one liter of sterile water having pH=2.8±0.05. The required dose is 65 mls of 2.8 pH PCI Buffer for every 100 mls of the 85 crit cell mass. In step 129, the centrifuge thoroughly mixes the solution during addition of PCI and them occasionally agitates the red blood cells and PCI mixture for about 10 minutes for equilibration to reduce the pH of the packed red blood cells from approx 7.0 to 5.5. Then, in step 123, the centrifuge expresses the separated waste (also called supernatant) while the red blood cells are left in the processing bag.

In step 131, the system purges the tubing with PEG and dispenses the calculated dose to the processing bag. In step 133, the system also adds enzymes to the processing bag, based on the amount of red blood cells measured in step 115. The enzyme includes 12.5 ml of rB-zyme or 25 ml of a suspension of exo- and endo- rA-zyme and the PEG dose is 23 ml per 250 ml of 85 crit cell suspension. The centrifuge agitates for 60 minutes at the incubation temperature of 26° C. for rB-zyme and at 37° C. for rA-zymes. The enzyme is suspended in 5.5 pH PCI Buffer, PEG is 1450 MW suspended in 5.5 pH PCI. The system also verifies the dose, the time and the temperature according to the algorithm (step 135) and continues the red blood cells conversion if all parameters are satisfied. Then, the system purges the tubing with saline and fills up the processing bag with saline. In step 123, the centrifuge spins the solution at 3000 RPM for about 2.5 minutes and then slows down to about 1500 RPM and expresses the supernatant waste while the washed red blood cells are left in the processing bag.

After the red blood cell conversion, the centrifuge expresses the supernatant (step 123). Next, in step 141, the system dispenses saline to the processing bag, agitates the mixture and spins the mixture at about 3000 RPM for about 2.5 minutes. The centrifuge expresses the waste, and the system restores the 85 crit cell mass. In step 145, purges the tubing with DPP to restore subsequently pH of converted red blood cells. In step 147, the system dispenses DPP by metering 110 ml of DPP Buffer for every 100 ml of the 85 cri cell suspension. The system dispenses 140 mM potassium phosphate dibasic with pH 9.0±0.1 (DPP) that includes potassium phosphate dibasic (anhydrous) 24.4 g/L suspended in one liter of sterile water. The centrifuge mixes thoroughly the liquid during addition of the buffer and equilibriates at 26° C. for 10 minutes also mixing occasionally during the equilibration. Next, in step 141, the system fills the processing bag with saline, agitates the mixture, and expresses the waste while the red blood cells are left in the processing bag.

Next, this system purges the lines with saline and washes the red blood cells several times by filling the processing bag with saline and subsequently expressing the waste (steps 141, 143 and 149). These steps remove the residual buffer, enzyme, PEG and phosphate to a level approximately equivalent to 99.9999%. After expressing the used saline in the last washing cycle (step 153), the system restores the 85 crit cell mass.

The controller directs fluid distribution module 40 to switch the tubing to collect the processed red blood cells in storage bag 74. This process is controlled by optical sensor 58 (shown in FIG. 3). After the optical sensor detects red blood cells, in step 155, the expresser pump reverses its pumping direction to draw back into the processing bag the red blood cells from the tubing located between the processing bag and the optical sensor. This is done to minimize the loss of red blood cells. Then, fluid distribution system 40 redirects the expressed red blood cells to storage bag 74. When the processing cycle is completed (step 157) the controller meters 100 mls of nutracell storage solution for 250 ml of the 85 crit cell suspension. This solution is then stored in the storage bag made from a material approved for 42-day storage (step 163).

This embodiment of the cell processing system is used for enzymatically converting blood type as described, for example, in U.S. Pat. Nos. 4,330,619, 4,427,777 and 4,609,627 by Goldstein.

Optical sensor 58 sensor monitors the color and the turbidity of the transferred fluids. Specifically, optical sensor 58 also monitors the supernatant expressed from the centrifuge chamber. In step 153, when red cells are detected in the supernatant, the controller responds by stopping the expressor pump to avoid losing any cells to waste. In step 155, the controller switches valves to collect the cells in cell storage container 74.

Optical sensor 58 is constructed and arranged to optically characterize a fluid being transferred within fluid distribution system 40. Since the processed cells must be maintained in a sterile environment during the entire process, the optical sensor has to satisfy the corresponding requirements. The requirements include a sterile and easily replaceable optical chamber. The entire design is waterproof and enables easy sterilization of all outside surfaces in accordance with the corresponding regulations.

In general, optical sensor 58 is constructed and arranged to perform in-line characterization of fluids being transferred during the operation of cell processing system 10. Optical sensor 58 periodically samples fluids flowing through an optical chamber and provides data to control module 80. When optical sensor 58 detects a selected quality of the optically sampled fluid, it provides the corresponding data to control module 80, which, in turn, activates a selected valve within fluid distribution system 40. The activated valve redirects the flow of the fluid in accordance with the process.

Figure 5:
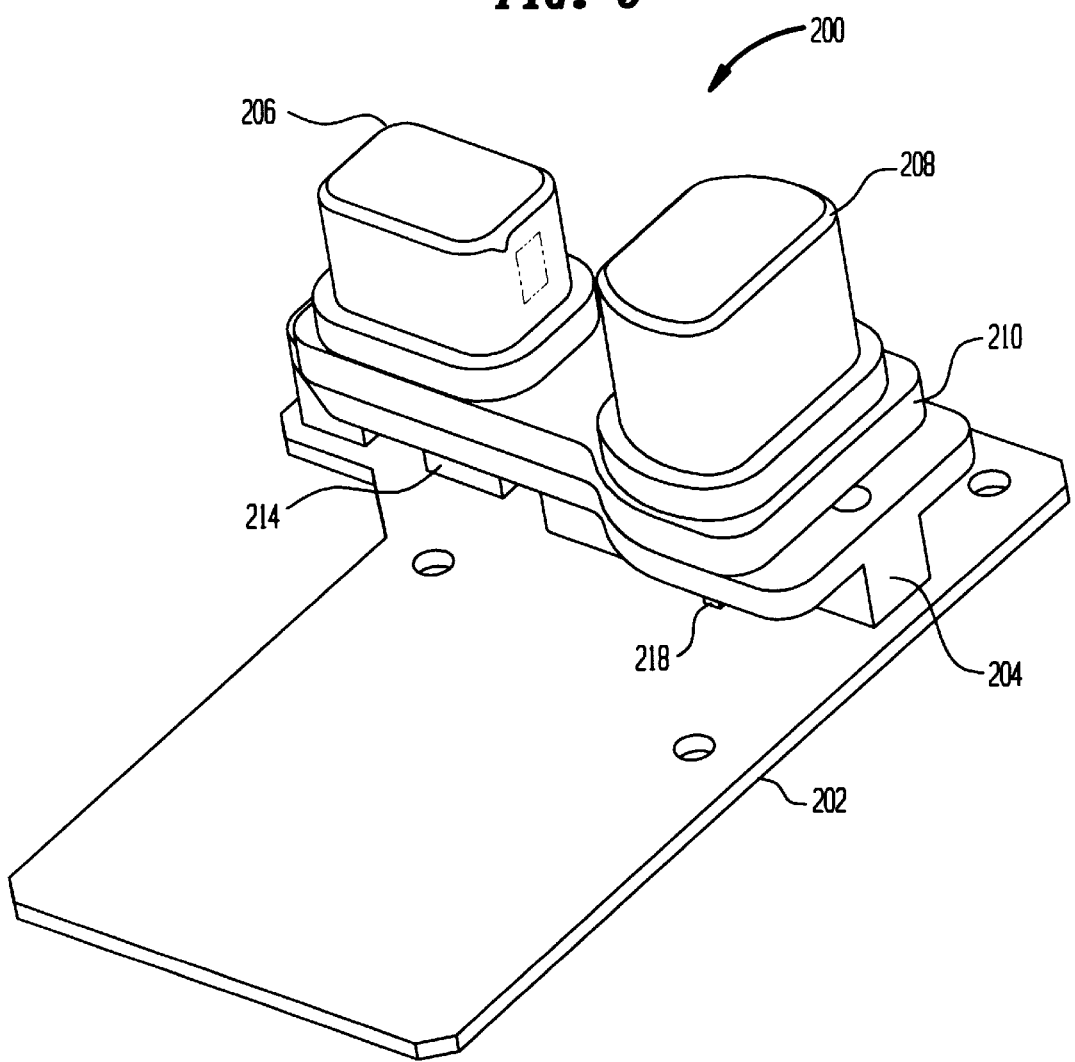
FIG. 5 is a perspective view of an optical sensor used in the cell processing system of FIG. 1.
Figure 6A:
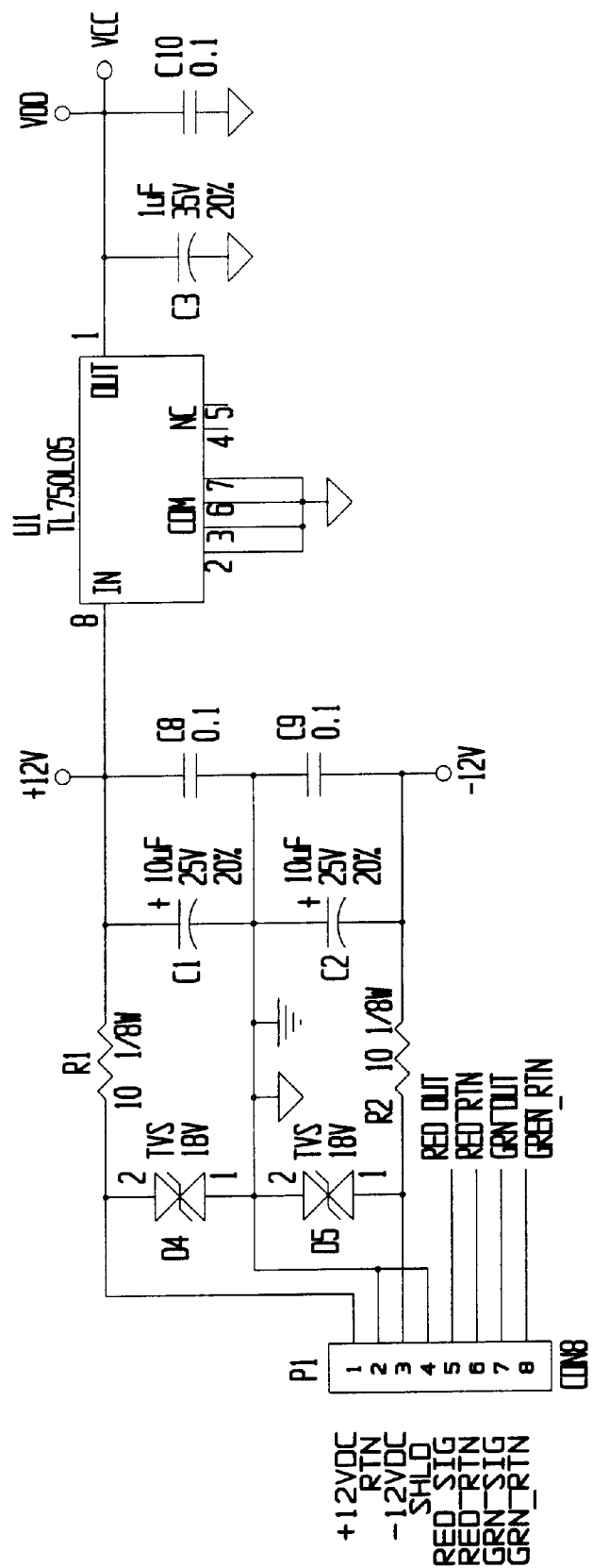
FIG. 6 is a schematic diagram of the elements used in optical sensor of FIG. 5.
Figure 6B:
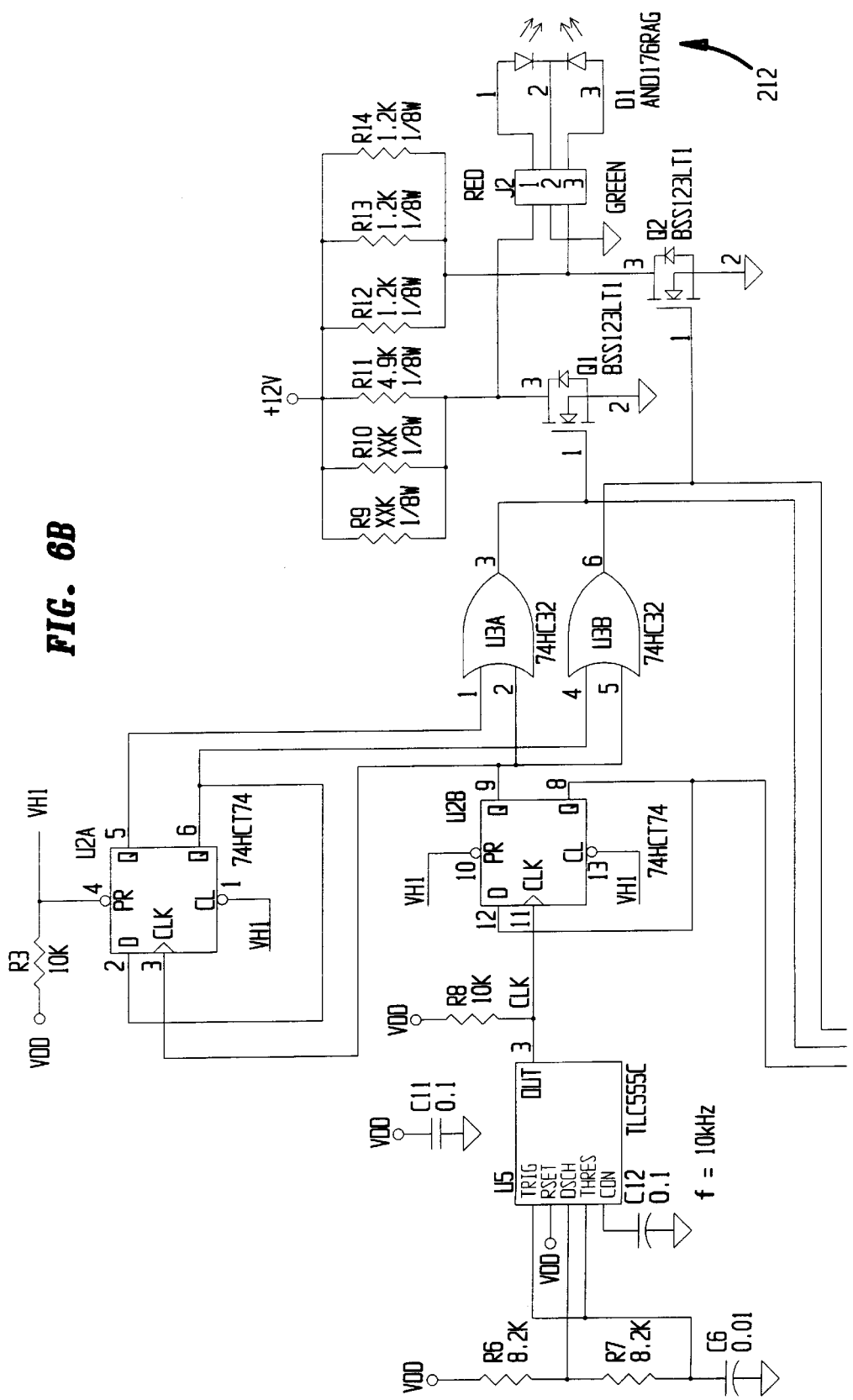
Figure 6C:
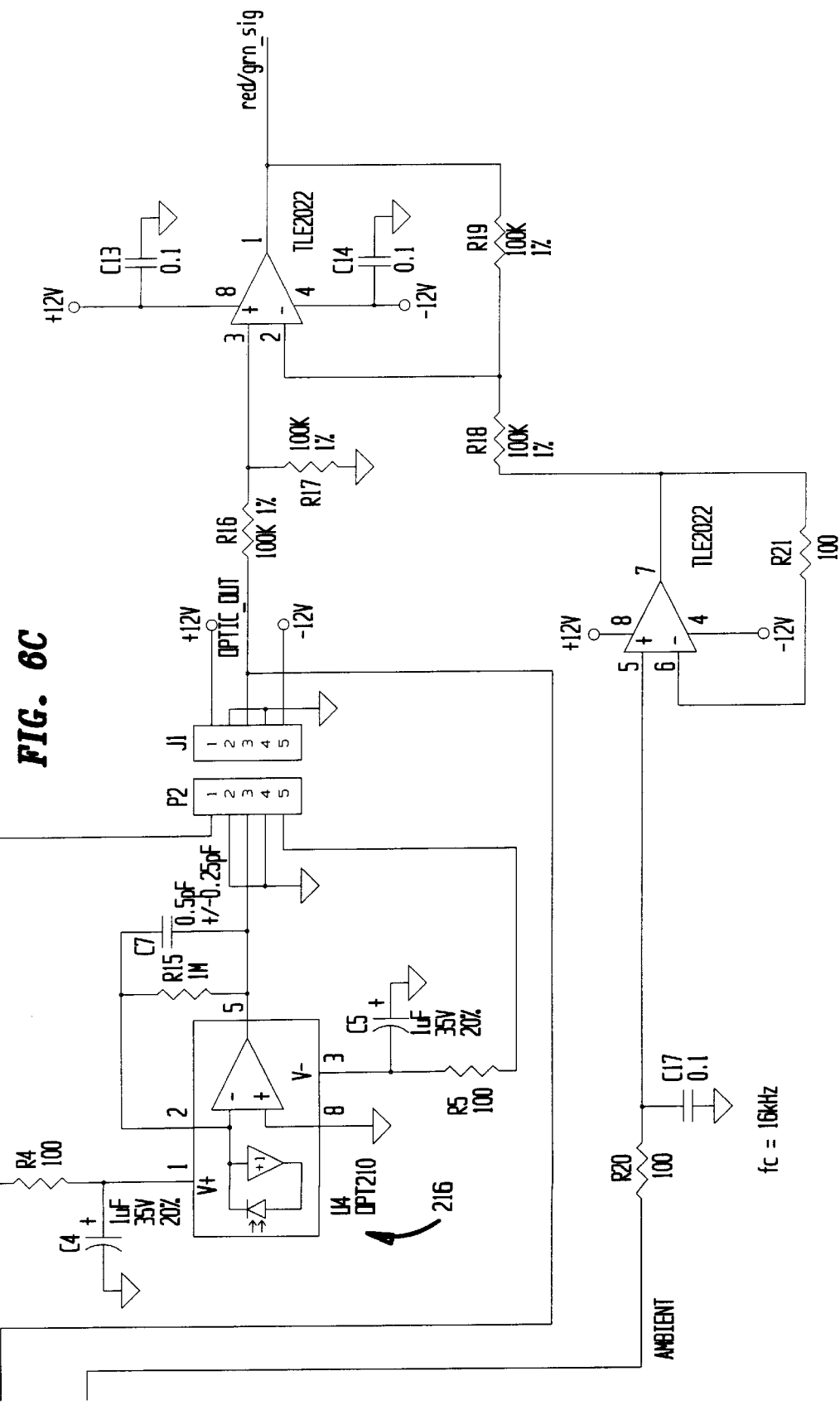
Figure 6D:
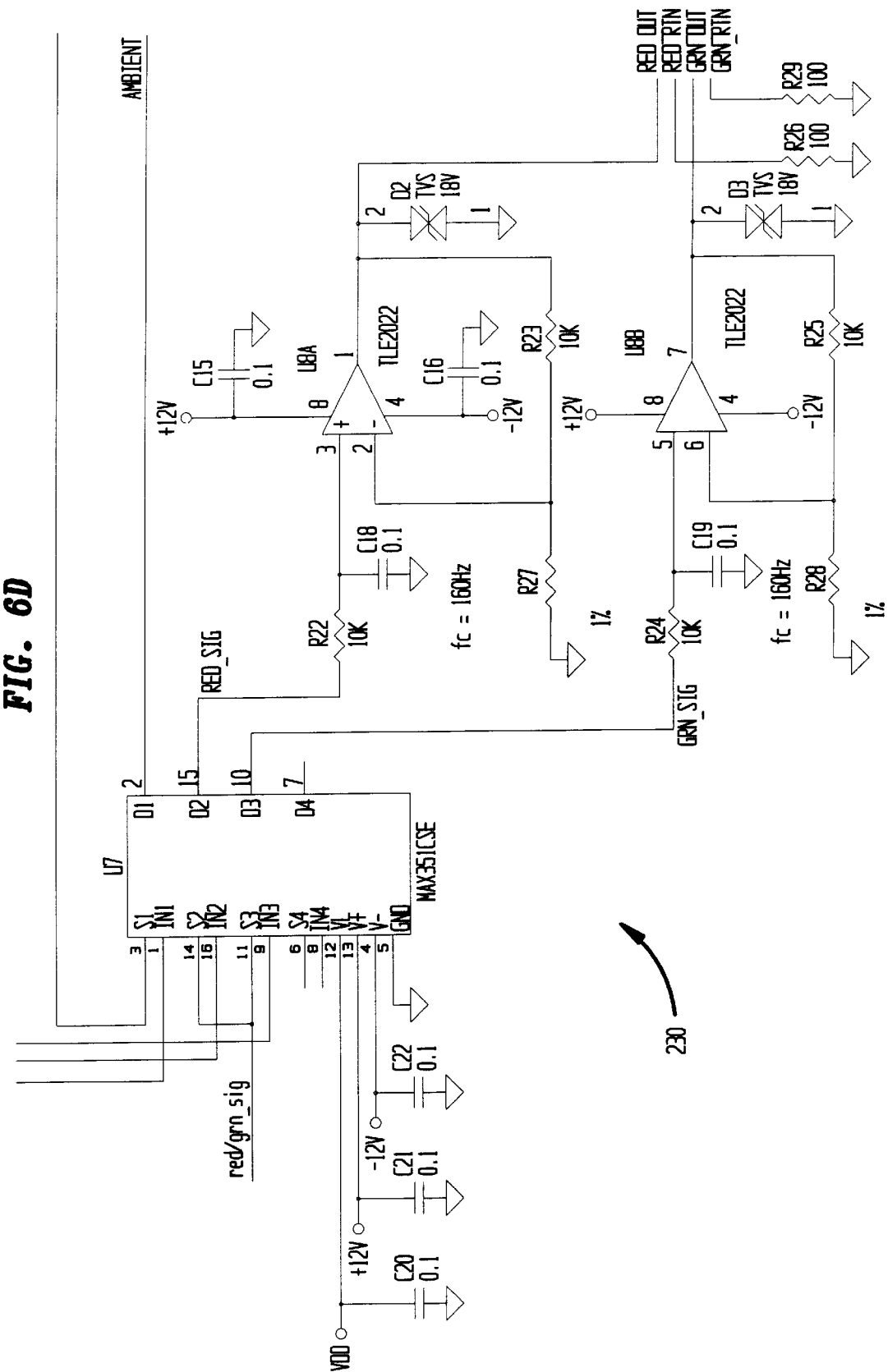

A specific, currently preferred embodiment of optical sensor 58 is shown in FIG. 5. Referring to FIG. 5, optical sensor 200 includes a circuit board 202, a plastic mount 204, a source cover 206, a detector cover 208 and a soft gasket 210. A two-color light emitting diode 212 (shown in FIG. 6) is mounted on a source mount 214 and placed inside source cover 206. A silicon diode detector 216 (shown in FIG. 6) is mounted on a detector mount 218 and is located within the detector cover 208. Also, mounted within source cover 206 is a source aperture having a 1 mm size hole. Source aperture 213, located in front of LED 212, is aligned with a detector aperture, also having a 1 mm hole, located in front of silicon diode detector 216.

The light emitting diode is constructed to emit light of about 560 nm and about 640 nm. Preferably, the LED is AND176RAG made by Purdy Electronics Corp., 720 Palomar Ave., Sunnyvale, Calif. The silicon diode detector is OPT210 made by Burr-Brown Corp., 6730 S. Tucson Blvd., Tucson, Ariz. 85706. Located on circuit board 202 is electronics 225 shown in FIG. 6.

After each power-up, control module 80 calibrates optical sensor 200 by taking the transmission data either without the cuvette or with the cuvette empty and comparing this to calibration data stored in the memory. Furthermore, a local controller 230 calibrates source 212 or detector 216 each time when a new cassette is located in fluid distribution system 40.

Figure 8:
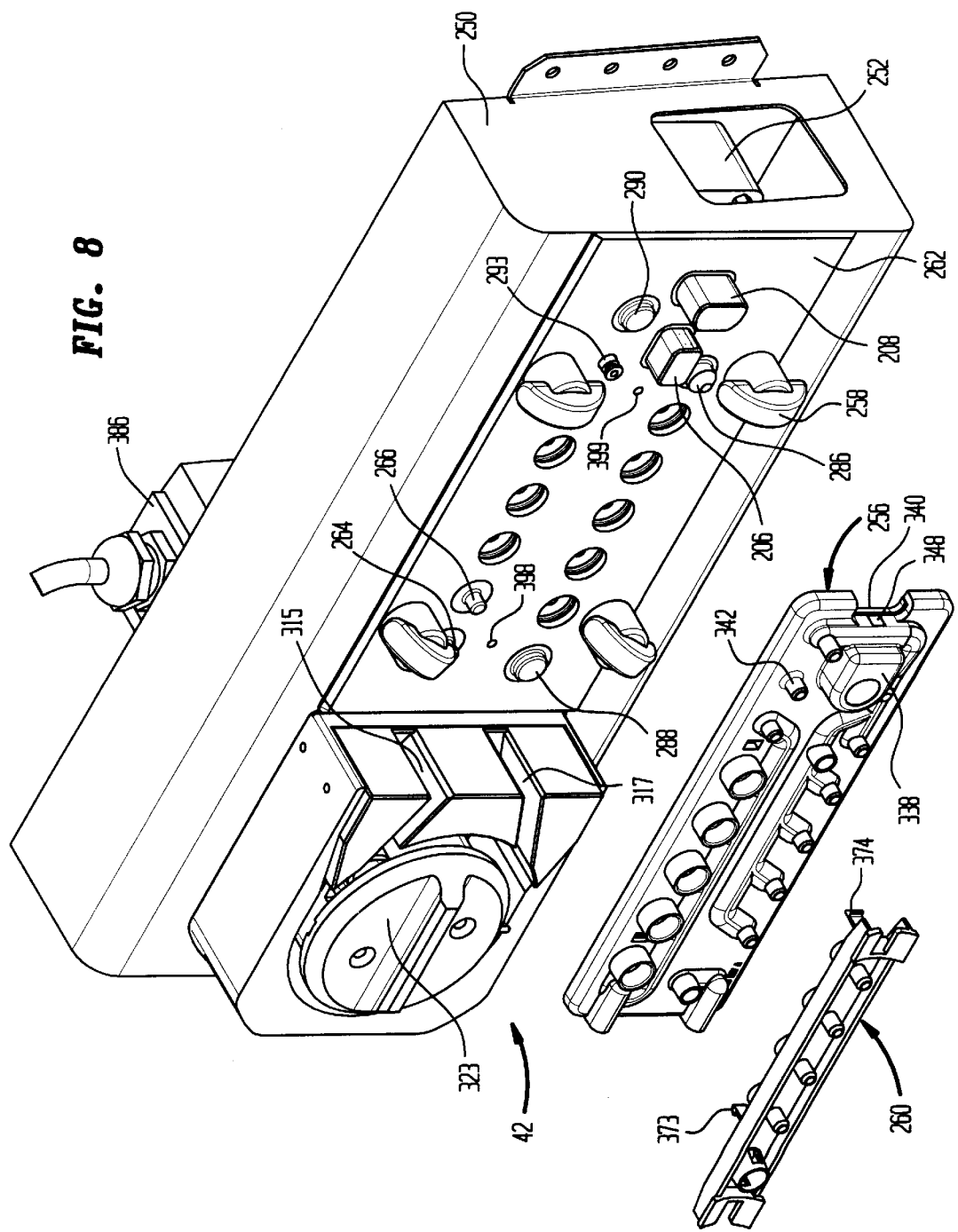
FIG. 8 is a partially exploded view of the fluid distribution module of FIG. 7 with another view of the optical sensor of FIG. 5.

FIGS. 7 and 8 show the arrangement of optical sensor 200 relative to fluid distribution module 40. The fluid distribution module is part of a fluid management system that coordinates the delivery of biological cells, process chemicals, solutions, fluids, reagents, etc. to conform with a processing algorithm executed by control module 80. Generally, the fluid distribution module controls the delivery of fluids from supply module 20 and cell module 12 to the processing module 60 (see FIGS. 1 and 3), as well as the expression of fluids from the processing module 60. The fluid distribution module is a device comprised of pumps, valves, pressure management devices, and other components useful in the management of a multiplicity of fluids.

Referring to FIGS. 7 and 8, the main components of the fluid distribution module are a housing 250, a pump valve assembly 252 mounted in the housing, and a distribution manifold 256 mounted on the housing on platen 262. The housing 252 can be formed from sheet metal. Also mounted on the housing 250 is peristaltic ("roller") pump 42. A connector 260 is attachable to the distribution manifold and receives tubing from different sources of fluids to be transferred to the manifold. The distribution manifold 256 includes a plurality of ports connected to interior runner channels for transferring fluid from one place to another. The manifold includes a series of interior channels connecting the ports in an arrangement for transference of the fluids from one port to another.

The distribution module 40 is arranged so that the distribution manifold 256 is easily attachable to the housing 252 so that it may be a single use disposable device which can be replaced after the processing cycle is complete for a bag 16 of biological cells. The distribution manifold 256 is easily attachable and detachable to the housing through the use of spring knobs 258 (see FIG. 8). To attach the manifold, the spring knobs are rotated horizontally, the manifold is placed on platen 262, the spring knobs are pulled out, rotated vertically and released to bias the manifold against the platen.

The platen 262 is seated in a recess 264 of housing 250. The platen 262 is an intermediary between the distribution manifold 256 and the pump valve assembly 252. The pump valve assembly includes a series of solenoids which can be energized to retract normally extended plungers associated with corresponding ports on the distribution manifold used to transfer fluids to and from the manifold 256, as explained in detail in the above-referenced co-pending U.S. patent application entitled "Fluid Management Systems".

Also supported by the pump valve assembly 252 are: load cells 288 and 290 which are used to sense the fluid pressure at two points within the distribution manifold 256; a sterile air hose and filter 293; and optical sensor 200 including a source housing 206 and a detector housing 208. Hall effect sensors 298 are used to detect the position of the plungers.

Platen 262 includes variously shaped holes 300 to accommodate the plungers 264–286, load cells 288 and 290, a source housing 206 and detector housing 208 of the optical sensor, and sterile air hose 293 (see FIGS. 7 and 8). To prevent fluids from possibly entering the pump valve assembly 252, individual silicon plunger membranes can be placed over each plunger, as well as the two load cells, and will seal the respective holes of the platen 262. Thus, the plungers 264 and 266 seen in FIG. 8 are covered by such membranes. In FIG. 8, plungers 264 and 266 are shown in the normal (i.e., non-energized) position in which the ports associated with the plungers 264–266 would be shut off. When attaching distribution manifold 256 to the platen 262 all of the solenoids are energized so the plungers do not interfere with the placement of the manifold. Furthermore, distribution manifold 256 provides a standardized position for optical cuvette 348 of optical sensor 200. Source housing 206 is received in cover 338 of distribution manifold 256, and detector housing 208 is received in recess 340 on the other side of cuvette 348.

All materials of distribution manifold 256 and optical sensor 200 are gamma stabile and resist color shift and physical property breakdown during gamma sterilization and have USP VI classification. The plastic components are made of an amorphous clear polymer with high flexural modulus and good impact strength because acrylic is not the only plastic with these properties. The possible materials include: polycarbonate (PC), styrene acrylonitrile (SAN), polyester and copolyester, clear acrylonitrile butadiene styrene (ABS), polystyrene (PC), polymethylpentene (TPX).) In the preferred embodiment, the plastic components are made of acrylic for its excellent light transmission, stiffness, and its ease of molding. They are processed by method of thermoplastic injection molding (IM). The optical cuvette 348 of distribution manifold 256 is molded to a finish standard of SPI A-1 (optical finish) as defined by The Society of Plastics Industry. Likewise, the mold cavity and core must have no draft in this area. The internal fluid channels require a finish of SPI B-3 or finer.

The sterility of all components is maintained during processing by aseptic methods and sterile pyrogen-free equipment and solutions. The transfer of all components is done without breakage of the seal.

Additional embodiments are within the following claims.

What is claimed is:

1. For use in an interactive cell processing system including a plurality of sensors arranged for monitoring and providing sensor data to a control module that directs processing of biological cells, said sensors including an optical sensor for characterizing a fluid transferred in a sterile manner during said processing, the optical sensor comprising:

a light source, connected to a control circuit, constructed and arranged to emit light of at least one selected wavelength directed toward said fluid;

a cuvette constructed as a part of a fluid distribution manifold that includes several conduits for transferring said sterile fluid during said processing, said cuvette being constructed and arranged to convey said fluid;

a light detector, connected to said control circuit, constructed and arranged to detect light emitted from said source and having interacted with said fluid flowing inside said cuvette; and said control circuit constructed and arranged to characterize said fluid in said cuvette based on said detected light wherein said light source and said light detector are located in a sealed housing constructed and arranged for wet cleaning.

2. For use in an interactive cell processing system including a plurality of sensors arranged for monitoring and providing sensor data to a control module that directs processing of biological cells, said sensors including an optical sensor for characterizing a fluid transferred in a sterile manner during said processing, the optical sensor comprising:

a light source, connected to a control circuit, constructed and arranged to emit light of at least one selected wavelength directed toward said fluid;

a cuvette constructed as a part of a fluid distribution manifold that includes several conduits for transferring said sterile fluid during said processing, said cuvette being constructed and arranged to convey said fluid;

a light detector, connected to said control circuit, constructed and arranged to detect light emitted from said source and having interacted with said fluid flowing inside said cuvette; and said control circuit constructed and arranged to characterize said fluid in said cuvette based on said detected light wherein said control circuit is constructed to activate said light source and said light detector to perform repeated measurements over a short period of time to increase precision of said characterization.

3. For use in an interactive cell processing system including a plurality of sensors arranged for monitoring and providing sensor data to a control module that directs processing of biological cells, said sensors including an optical sensor for characterizing a fluid transferred in a sterile manner during said processing, the optical sensor comprising:

a light source, connected to a control circuit, constructed and arranged to emit light of at least one selected wavelength directed toward said fluid;

a cuvette constructed as a part of a fluid distribution manifold that includes several conduits for transferring said sterile fluid during said processing, said cuvette being constructed and arranged to convey said fluid;

a light detector, connected to said control circuit, constructed and arranged to detect light emitted from said source and having interacted with said fluid flowing inside said cuvette; and said control circuit constructed and arranged to characterize said fluid in said cuvette based on said detected light wherein said control circuit is constructed to calibrate operation of said optical sensor after placement of said cuvette.

4. For use in an interactive cell processing system including a plurality of sensors arranged for monitoring and providing sensor data to a control module that directs processing of biological cells, said sensors including an optical sensor for characterizing a fluid transferred in a sterile manner during said processing, the optical sensor comprising:

a light source, connected to a control circuit, constructed and arranged to emit light of at least one selected wavelength directed toward said fluid;

a cuvette constructed as a part of a fluid distribution manifold that includes several conduits for transferring said sterile fluid during said processing, said cuvette being constructed and arranged to convey said fluid;

a light detector, connected to said control circuit, constructed and arranged to detect light emitted from said source and having interacted with said fluid flowing inside said cuvette; and said control circuit constructed and arranged to characterize said fluid in said cuvette based on said detected light, the sensor being further arranged to provide data to said control module to actuate redistribution of fluids flowing in said conduits.

\* \* \* \* \*